(12) United States Patent
Fei et al.

(10) Patent No.: US 9,370,475 B2
(45) Date of Patent: Jun. 21, 2016

(54) ORAL CARE COMPOSITIONS

(75) Inventors: Lin Fei, Kendall Park, NJ (US);
Stanislav Jaracz, Somerset, NJ (US);
Ying Yang, Monmouth Junction, NJ
(US); Guofeng Xu, Plainsboro, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/360,049

(22) PCT Filed: Dec. 2, 2011

(86) PCT No.: PCT/US2011/063031
§ 371 (c)(1),
(2), (4) Date: May 22, 2014

(87) PCT Pub. No.: WO2013/081627
PCT Pub. Date: Jun. 6, 2013

(65) Prior Publication Data
US 2014/0314688 A1 Oct. 23, 2014

(51) Int. Cl.
*A61Q 11/00* (2006.01)
*A61K 36/575* (2006.01)
*A61K 36/57* (2006.01)
*A61K 8/34* (2006.01)

(52) U.S. Cl.
CPC .................. *A61K 8/347* (2013.01); *A61K 36/57* (2013.01); *A61K 36/575* (2013.01); *A61Q 11/00* (2013.01); *A61K 2800/49* (2013.01); *A61K 2800/5922* (2013.01)

(58) Field of Classification Search
None
See application file for complete search history.

(56) References Cited

U.S. PATENT DOCUMENTS

| | | | |
|---|---|---|---|
| 2006/0127329 A1* | 6/2006 | Xu et al. | .......................... 424/57 |
| 2006/0140880 A1 | 6/2006 | Subramanyam | |
| 2008/0095719 A1* | 4/2008 | Herrmann | ................ A61K 8/97 424/48 |
| 2014/0356299 A1 | 12/2014 | Fei et al. | |

FOREIGN PATENT DOCUMENTS

| | | |
|---|---|---|
| JP | 07033649 A * | 2/1995 |
| JP | 2008-007433 A | 1/2008 |
| JP | 2008-007436 A | 1/2008 |
| WO | WO 01/82922 | 11/2001 |
| WO | WO 01/85116 | 5/2002 |
| WO | WO 2010/042313 | 4/2010 |
| WO | WO 2011/106492 | 9/2011 |
| WO | WO 2011/106493 | 9/2011 |
| WO | WO 2011/131439 | 10/2011 |

OTHER PUBLICATIONS

International Search Report and the Written Opinion issued in International Application PCT/US2011/063031 mailed Oct. 9, 2012. WO.

* cited by examiner

*Primary Examiner* — Frederick Krass
*Assistant Examiner* — Tracy Liu

(57) ABSTRACT

Oral care compositions comprising isobutyl magnolol and n-butyl magnolol. A method of enhancing the solubility of isobutyl magnolol in an oral care composition comprises admixing n-butyl magnolol with an orally acceptable carrier comprising isobutyl magnolol. The composition may be used to treat diseases or conditions of the oral cavity such as caries, gingivitis, periodontitis, tooth yellowing and halitosis.

15 Claims, No Drawings

ORAL CARE COMPOSITIONS

CROSS-REFERENCE TO RELATED PATENT APPLICATIONS

The present application is a U.S. national stage entry under 35 U.S.C. §371 of Patent Cooperation Treaty Patent Application No. PCT/US2011/63031, filed Dec. 2, 2011, the entirety of which is incorporated herein by reference.

BACKGROUND

There is a need for safe, effective antibacterial and anti-inflammatory agents for use in oral care compositions. Magnolia extract is known to contain compounds having antibacterial and/or anti-inflammatory properties, and such compounds have been the focus of considerable interest for use in oral care compositions. The use of such compounds in oral care compositions is described, for example, in WO2001/085116, WO 2011/106492 and WO 2011/106493, the contents of which application are incorporated herein by reference. Synthetic non-natural analogs of various components of magnolia extract are also known to have antibacterial activity. Isobutyl magnolol (5,5'-di(2-methylpropyl)-biphenyl-2,2'-diol) is a promising anti-bacterial and anti-inflammatory active for oral care use. Synthesis of this compound, but not its use for oral care indications, is described in WO2010/042313. However, the extremely poor solubility of isobutyl magnolol both in water and in oil, and its strong tendency to crystallize out from the composition matrix in a variety of surfactant systems have made its use in oral care formulations undesirable. Thus, there is a need for oral care compositions that are both orally acceptable and capable of solubilizing isobutyl magnolol.

SUMMARY

It is now surprisingly discovered that adding n-butyl magnolol to a composition comprising isobutyl magnolol greatly enhances the solubility of the isobutyl magnolol in the composition.

Without being bound by them, we hypothesize that the poor solubility of isobutyl magnolol compared to its other analogs is due to its high crystallization energy. By blending with butyl magnolol, the tendency of crystallizing out is significantly reduced. Thus, the solubility is increased and the uptake is increased. The inventors have found that the optimal mixing ratio between isobutyl magnolol and n-butyl magnolol is 1:1 when no cosolvent such as propylene glycol monocaprylate is added. When a propylene glycol monoester, e.g., propylene glycol monocaprylate is added, the optimal ratio becomes 3:1. In comparison, the uptake of butyl magnolol is also reported. The uptake increases with the increase of butyl magnolol in the formula.

In one embodiment, therefore, the invention provides an oral care composition, for example a toothpaste, comprising isobutyl magnolol and n-butyl magnolol, as well as methods of making and using such compositions.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The following description of the preferred embodiment(s) is merely exemplary in nature and is in no way intended to limit the invention, its application, or uses.

In a first embodiment, the invention, provides an oral care composition (Composition 1), for example a toothpaste, comprising isobutyl magnolol and n-butyl magnolol. For example, the invention provides oral care compositions as follows:

1.1. Composition 1 in the form of a toothpaste;
1.2. Composition 1 in the form of a mouthrinse;
1.3. Any of the foregoing compositions wherein the isobutyl magnolol is present in an antibacterially effective concentration;
1.4. Any of the foregoing compositions comprising an antibacterially effective amount of isobutyl magnolol and an amount of n-butyl magnolol effective to solubilize the isobutyl magnolol in an orally acceptable carrier;
1.5. Any of the foregoing compositions wherein the concentration of isobutyl magnolol is from 0.1-3%, e.g., about 0.5-2%, based on the total weight of the composition;
1.6. Any of the foregoing compositions wherein the ratio by weight of isobutyl magnolol to n-butyl magnolol is from 1:3 to 3:1;
1.7. Any of the foregoing compositions wherein the ratio by weight of isobutyl magnolol to n-butyl magnolol is about 1:1.;
1.8. Any of the foregoing compositions farther comprising a fatty acid monoester of propylene glycol, e.g., propylene glycol monocaprylate, e.g., in a ratio by weight of 0.25:1 to 3:1, e.g. about 1:1 relative to, the total weight of the of isobutyl magnolol and n-butyl, magnolol;
1.9. Any of the foregoing compositions further comprising polyethylene glycol, e.g., PEG 600, e.g., in an amount of 0.5-5% by weight;
1.10. Any of the foregoing compositions further comprising a humectant, e.g., glycerin, sorbitol, or mixtures thereof, e.g., in an amount by weight of about 30%-70%, e.g., 40-60%, e.g., about 50%;
1.11. Any of the foregoing compositions further comprising an anionic surfactant, e.g., sodium lauryl sulfate, e.g., in an amount of 0.5-5%, e.g., about 2.5%;
1.12. Any of the foregoing compositions further comprising an effective amount of a fluoride ion source, e.g., sodium fluoride, e.g., in an amount by weight of 0.1-0.5%, e.g., about 0.34%;
1.13. Any of the foregoing compositions further comprising flavoring, e.g., selected from non-caloric sweeteners, e.g., saccharine, herbal flavorings (e.g., mint flavor), and combinations thereof;
1.14. Any of the foregoing compositions further comprising an abrasive material, e.g., silica abrasive, precipitated calcium carbonate, or combinations thereof;
1.15. Any of the foregoing compositions comprising the following ingredients:

| Ingredient | % by weight |
| --- | --- |
| PEG600 | 2-5%, e.g., about 4.2% |
| Flavor | 0-3%, e.g., about 1.4% |
| Isobutyl magnolol | 0.5-3%, e.g., about 0.7% |
| n-butyl magnolol | 0.5-3%, e.g., about 0.7% |
| Glycerin | 20-30%, e.g., about 25% |
| Sorbitol | 20-30%, e.g., about 25% |
| Sodium Saccharine | 0.1-0.7%, e.g., about 0.4% |
| Sodium Fluoride | 0.1-0.7%, e.g., about 0.34 |
| Sodium lauryl sulfate (SLS) | 1-3%, e.g., about 2.5% |
| Water | As required for suitable consistency |
| Abrasive silica | 0-20% |

As used herein, the term. "solubilizing effective amount" refers to the amount of an ingredient effective to sufficiently solubilize the amount of isobutyl magnolol present in an orally acceptable carrier.

In a further embodiment, the invention provides a method of treatment, prophylaxis or control of a disease or condition of the oral cavity, for example a bacterial infection or inflammatory condition in the mouth, for example gingivitis, comprising applying an oral care composition in accordance with the invention, e.g., Composition 1, et seq., to the oral cavity of a patient in need thereof. In some embodiments, the disease or condition of the oral cavity includes a disease or condition of the teeth, oral mucosa, gingiva or tongue. Such diseases or conditions include caries, gingivitis, periodontitis and cosmetic conditions such as yellowing and malodour.

In a further embodiment, the invention provides the use of n-butyl magnolol and isobutyl magnolol in combination for the manufacture of an oral care composition, e.g., according to Composition 1 et seq.,. for such a method of treatment, prophylaxis or control of a disease or condition of the oral cavity.

In a further embodiment, the invention provides a method of making an oral care composition, e.g., according to Composition 1., et seq., comprising admixing n-butyl magnolol and isobutyl magnolol with an orally acceptable carrier.

The methods and compositions of the present embodiments impart advantages over the prior art compositions by providing an oral composition that is well solubilized, safe, and highly efficacious against bacterial infection and/or inflammation in a mammalian subject.

Magnolol (5,5'-di(prop-2-en-1-yl)-biphenyl-2,2'-diol) is a bioactive compound found in the bark of the Houpu magnolia (*Magnolia officinalis*). Isobutyl magnolol (5,5'-di,(2-methylpropyl)-biphenyl-2,2'-diol) is a synthetic derivative of magnolol, with antibacterial and anti-inflammatory properties, having a structure as follows:

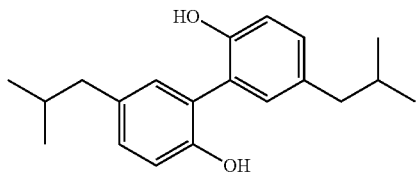 [SMILES: CC(C)Cc1ccc(O)c(-c2cc(CC(C)C)ccc2O)c1]

n-Butyl magnolol (5,5'-dibutyl-biphenyl-2,2'-diol) is the analogous compound with two n-butyl moieties in lieu of the isobutyl moieties.

By "orally acceptable" is meant safe for use in the mouth at levels required. In general, all components of the compositions of the present invention are orally acceptable.

The expressions "carrier" or "aqueous carrier" or "orally acceptable carrier" as used throughout this description denote any safe and effective materials for use herein. Such materials include, water, solvents, etc., that may contain a humecant such as glycerin, sorbitol, xylitol and the like. The carrier or orally acceptable carrier also may include additional dentifrice components, such as thickening agents, ionic active ingredients, buffering agents, anticalculus agents, abrasive polishing materials, peroxide sources, alkali metal bicarbonate salts, surfactants, titanium dioxide, coloring agents, flavor systems, sweetening agents, antimicrobial agents, herbal agents, desensitizing agents, stain reducing agents, and mixtures thereof.

Orally acceptable carriers for use in the invention include the conventional and known carriers used in making toothpastes, tooth powders, prophylaxis pastes, mouth rinses, lozenges, gums, beads, and the like, and are more fully described hereinafter. It is preferred that the orally acceptable carrier does not cause irritation, swelling or pain and does not typically produce an allergic or untoward reaction such as gastric upset, nausea or dizziness. Selection of specific carrier components is dependant on the desired product form, including dentifrices, toothpastes, tooth powders, prophylaxis pastes, mouth rinses, lozenges, gums, gels, paints, confectionaries, and the like.

The term "mouthrinse" in the present invention refers to oral compositions that are substantially liquid in character, such as a mouth wash, spray, or rinse. In such a preparation the orally acceptable carrier typically has an aqueous phase comprising water or a water and alcohol mixture. Further, in various embodiments, the oral carrier includes a humectant and surfactant as described below. Generally, the weight ratio of water to alcohol is in the range of in an amount of 1:1 to 20:1, preferably 3:1 to 10:1 and More preferably 4:1 to 6:1. The total amount of water- alcohol mixture in this type of preparation is typically in an amount of 70 to 99.9% of the preparation. In various embodiments, the alcohol is typically ethanol or isopropanol.

As recognized by one of skill in the art, the orally acceptable carrier of the present invention may also comprise a variety of other conventional active ingredients known to one of skill in the art, including anti-plaque agents, whitening agents, antibacterial agents, tartar control (anticalculus) agent, anti-caries agents, sensitivity agents, and the like. Preferably, the carrier does not substantially reduce the efficacy of the isobutyl magnolol.

The pH of such liquid and other preparations of the oral composition. of the present invention is generally in an amount of 4.5 to 10. The pH can be controlled with acid (e.g., citric acid or benzoic acid) or base (e.g., sodium hydroxide) or buffered (with sodium citrate, benzoate, carbonate, or bicarbonate, disodium hydrogen phosphate, or sodium dihydrogen phosphate, for example).

In various embodiments, the aqueous oral composition (e.g., mouthrinse) contains a humectant. The humectant is generally a mixture of humectants, such as glycerin and sorbitol, and a polyhydric alcohol such as hexylene glycol, or polyethylene glycol, although the use of polyethylene glycol as a humectant in addition to its use to enhance the solubility of the active ingredient is optional. The humectant content for a mouth rinse typically is in the range of 5 to 40% and preferably 10 to 30%.

Surfactants suitable for compositions of the present invention include anionic, nonionic, and zwitterionic surfactants. The surfactant usually is present in the aqueous oral compositions of the present invention in an amount of 0.01% to 5%, preferably in an amount of 0.5% to 2.5%.

The oral composition according to. the present invention may optionally include other materials, such as for example, cleaning agents, flavouring agents, sweetening agents, adhesion agents, surfactants, foam modulators, abrasives, pH modifying agents, humectants, moisturizers, mouth feel agents, colorants, abrasives, preservatives, fluoride ion source, saliva stimulating agents, emollients, viscosity modifiers, diluents, emulsifiers, nutrients and combinations thereof. Various components that may be added to the oral composition include, for example, a sweetening agent such as saccharin, or sodium saccharin, alcohols such as ethanol, fluoride ion sources such as sodium fluoride, as well as glycerine, sorbitol, polyethylene glycols, Poloxomer polymers such as POLOXOMER®407, PLURONIC®F108, (both available from BASF Corporation), alkyl polyglycoside (APG), polysorbate, PEG40, castor oil, menthol, and the like. It is understood that while general attributes of each of the above categories of materials may differ, there may be some common attributes and any given material may serve multiple purposes within two or more of such categories of materials. Preferably, such carrier materials are selected for compatibility with the active ingredients found in magnolia extract or synthetic analogues thereof, as well as with other ingredients of the composition.

Flavorants among those useful herein include any material or mixture of materials operable to enhance the taste of the composition. Any orally acceptable natural or synthetic flavorant can be used, such as flavoring oils, flavoring aldehydes, esters, alcohols, similar materials, and combinations thereof. Flavorants include vanillin, sage, marjoram, parsley oil, spearmint oil, cinnamon oil, oil of wintergreen (methylsalicylate), peppermint oil, clove oil, bay oil, anise oil, eucalyptus oil, citrus oils, fruit oils and essences including those derived from lemon, orange, lime, grapefruit, apricot, banana, grape, apple, strawberry, cherry, pineapple, etc., bean- and nut-derived flavors such as coffee, cocoa, cola, peanut, almond, etc., adsorbed and encapsulated flavorants, and mixtures thereof. Also encompassed within flavorants herein are ingredients that provide fragrance and/or other sensory effect in the mouth, including cooling or warming effects. Such ingredients include menthol, menthyl acetate, menthyl lactate, camphor, eucalyptus oil, eucalyptol, anethole, eugenol, cassia, oxanone, [alpha]-irisone, propenyl guaiethol, thymol, linalool, benzaldehyde, cinnamaldehyde, N-ethyl-p-menthan-3-carboxamine, N,2,3-trimethyl-2-isopropylbutanamide, 3-1-menthoxypropane-1,2-diol, cinnamaldehyde glycerol acetal (CGA), methone glycerol acetal (MGA), and mixtures thereof. One or more flavorants are optionally present in a total amount of 0.01% to 5%, optionally in various embodiments from 0.05 to 2%, from 0.1% to 2.5%, and from 0.1 to 0.5%.

Sweetening agents among those useful herein include dextrose, polydextrose, sucrose, maltose, dextrin, dried invert sugar, mannose, xylose, ribose, fructose, levulose, galactose, corn syrup, partially hydrolyzed starch, hydrogenated starch hydrolysate, sorbitol, mannitol, xylitol, isomalt, aspartame, neotame, saccharin and salts thereof, sucralose, dipeptide-based intense sweeteners, cyclamates, dihydrochalcones, and mixtures thereof.

Mouth-feel agents include materials imparting a desirable texture or other feeling during use of the composition of the invention.

Colorants among those useful herein include pigments, dyes, lakes and agents imparting a particular luster or reflectivity such as pearling agents. In various embodiments, colorants are operable to provide a white or light-colored coating on a dental surface, to act as an indicator of locations on a dental surface that have been effectively contacted by the composition, and/or to modify appearance, in particular color and/or opacity, of the composition to enhance attractiveness to the consumer. Any orally acceptable colorant can be used, including FD&C dyes and pigments, talc, mica, magnesium carbonate, calcium carbonate, magnesium silicate, magnesium aluminum silicate, silica, titanium dioxide, zinc oxide, red, yellow, brown and black iron oxides, ferric ammonium ferrocyanide, manganese violet, ultramarine, titaniated mica, bismuth oxychloride, and mixtures thereof One or more colorants are optionally present in a total amount of 0.001% to 20%, for example 0.01% to 10% or 0.1% to 5%.

In some embodiments, the oral care compositions of the present invention may comprise an optional abrasive useful for example as a polishing agent. Any orally acceptable abrasive can be used, but type, fineness, (particle size) and amount of abrasive should he selected so that tooth enamel is not excessively abraded in normal use of the composition. Suitable optional abrasives include silica, for example in the form of precipitated silica or as admixed with alumina, insoluble phosphates, calcium carbonate, and mixtures thereof. Among insoluble phosphates useful as abrasives are orthophosphates, polymetaphosphates and pyrophosphates. Illustrative examples are dicalcium orthophosphate dihydrate, calcium pyrophosphate, calcium pyrophosphate, tricalcium phosphate, calcium polymetaphosphate and insoluble sodium polymetaphosphate.

In some embodiments, the compositions of the present invention optionally comprise a tartar control (anticalculus) agent. Tartar control agents among those useful herein include salts of any of these agents, for example their alkali metal and ammonium salts: phosphates and polyphosphates (for example pyrophosphates), polyaminopropanesulfonic acid (AMPS), polyolefin sulfonates, polyolefin phosphates, diphosphonates such as azacycloalkane-2,2-diphosphonates (e.g., azacycloheptane-2,2-diphosphonic acid), N-methyl azacyclopentane-2,3-diphosphonic acid, ethane-1-hydroxy-1,1-diphosphonic acid (EHDP) and ethane-1-amino-1,1-diphosphonate, phosphonoalkane carboxylic acids and. Useful inorganic phosphate and polyphosphate salts include monobasic, dibasic and tribasic sodium phosphates, sodium tripolyphosphate, tetrapolyphosphate, mono-, di-, tri- and tetrasodium pyrophosphates, sodium trimetaphosphate, sodium hexametaphosphate and mixtures thereof.

In other embodiments, the oral compositions of the present invention optionally comprise a fluoride ion source, useful, for example, as an anti-caries agent. Any orally acceptable fluoride ion source can be used, including potassium, sodium and ammonium fluorides and monofluorophosphates, stannous fluoride, indium fluoride, amine fluorides such as olaflur (N'-octadecyltrimethylendiamine-N,N,N'-tris(2-ethanol)-dihydrofluoride), and mixtures thereof. One or more fluoride ion sources are optionally present in an amount providing a clinically efficacious amount of soluble fluoride ion to the oral composition.

in further embodiments, the oral compositions of the present invention optionally comprise a saliva stimulating agent useful, for example, in amelioration of dry mouth. Any orally acceptable saliva stimulating agent can be used, including without limitation food acids such as citric, lactic, malic, succinic, ascorbic, adipic, fumaric and tartaric acids, and mixtures thereof. One or more saliva stimulating agents are optionally present in saliva stimulating effective total amount.

In yet other embodiments, the oral compositions of the present invention optionally comprise a nutrient. Suitable nutrients include vitamins, minerals, amino acids, and mixtures thereof. Vitamins include Vitamins C and D, thiamine, riboflavin, calcium pantothenate, niacin, folic acid, nicotinamide, pyridoxine, cyanocobalamin, para-aminobenzoic acid, bioflavonoids, and mixtures thereof. Nutritional supplements include amino acids (such as L-tryptophane, L-lysine, methionine, threonine, levocarnitine and L-carnitine), lipotropics (such as choline, inositol, betaine, and linoleic acid), and mixtures thereof.

In some embodiments, the present invention provides a method of treating conditions associated with the presence of oral bacteria comprising providing an oral composition in accordance with any of the above-described embodiments, and applying the oral composition to the oral cavity of the mammalian subject. In some embodiments, the method comprises repeating the application of the composition Multiple times until the desired anti-bacterial and/or anti-inflammatory effects are achieved in the subject.

As referred to herein, "inflammation" of the oral tissue generally refers to a localized protective response elicited by injury or destruction of tissues, which serves to destroy, dilute, or sequester both the injurious agent and the injured tissue. In the acute form, it is characterized by pain, heat, redness, swelling, and loss of function. Chronic inflammation is a slow process and primarily characterized by the formation of new connective tissue. Chronic inflammation is often a continuation of acute inflammation or a prolonged low-grade form of inflammation (such as that associated with periodontitis or gingivitis) and usually causes permanent tissue damage. Histologically, inflammation involves a complex series of events, including dilation of arterioles, capillaries, and venules, with increased permeability and blood flow; exudation of fluids, including plasma proteins, and leukocytic migration into the inflammatory locus. Inflammation corresponds to enhanced levels of proinflammatory cellular mediators, or substances that are released from cells, for example, as the result of the interaction of an antigen with an antibody or by the action of antigen with a sensitized lymphocyte.

In various embodiments, application or contacting is accomplished by rinsing, coating, brushing, or layering using appropriate dressing materials. In some embodiments, contacting also includes incidental contact during eating or chewing. In various embodiments, application of the composition comprises the use of an application device which aids in maintaining the contact time of the anti-inflammatory active ingredient comprising magnolia extract to the target tissue for a sufficient time as to allow the pharmacological inhibition of the elevated production of one or more inflammatory mediators, such as PGE 2 and TNF-α.

In certain embodiments, an oral composition is not intentionally swallowed, but rather is retained in the oral cavity for a time sufficient to affect the intended utility. In other embodiments, particularly those where the oral composition is provided in an animal product, such as a pet food, pet food supplement (e.g., a treat), or a chew toy, the oral composition may be ingested at small concentrations which are not harmful to the animal. Preferably, specific materials and compositions to be used in this invention are pharmaceutically- or cosmetically-acceptable.

As used throughout, ranges are used. as shorthand for describing each and every value that is within the range. Any value within the range can be selected as the terminus of the range. In addition, all references. cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLES

Example 1

Compositions with different combinations of isobutyl magnolol and n-butyl magnolol in ratios of 1:3, 1:1 and 3:1 are prepared as shown in Table 1 (below):

TABLE 1

|  | 1 | 2 | 3 | 4 | 5 | 6 | 7 | 8 | 9 | 10 |
| --- | --- | --- | --- | --- | --- | --- | --- | --- | --- | --- |
| PEG600 | 4.2 | 4.2 | 4.2 | 4.2 | 4.2 | 2.8 | 2.8 | 2.8 | 2.8 | 2.8 |
| Flavor | 1.4 | 1.4 | 1.4 | 1.4 | 1.4 | 1.4 | 1.4 | 1.4 | 1.4 | 1.4 |
| IBM | 1.4 | 1.05 | 0.7 | 0.35 |  | 1.4 | 1.05 | 0.7 | 0.35 |  |
| n-BM |  | 0.35 | 0.7 | 1.05 | 1.4 |  | 0.35 | 0.7 | 1.05 | 1.4 |
| PGMC |  |  |  |  |  | 1.4 | 1.4 | 1.4 | 1.4 | 1.4 |
| Glycerin | 25.22 | 25.22 | 25.22 | 25.22 | 25.22 | 25.22 | 25.22 | 25.22 | 25.22 | 25.22 |
| Sorbitol | 24.94 | 24.94 | 24.94 | 24.94 | 24.94 | 24.94 | 24.94 | 24.94 | 24.94 | 24.94 |
| Sodium Saccharine | 0.42 | 0.42 | 0.42 | 0.42 | 0.42 | 0.42 | 0.42 | 0.42 | 0.42 | 0.42 |
| Sodium Fluoride | 0.34 | 0.34 | 0.34 | 0.34 | 0.34 | 0.34 | 0.34 | 0.34 | 0.34 | 0.34 |
| SLS | 2.52 | 2.52 | 2.52 | 2.52 | 2.52 | 2.52 | 2.52 | 2.52 | 2.52 | 2.52 |
| Water | 39.55 | 39.55 | 39.55 | 39.55 | 39.55 | 39.55 | 39.55 | 39.55 | 39.55 | 39.55 |
| Total | 100 | 100 | 100 | 100 | 100 | 100 | 100 | 100 | 100 | 100 |

IBM = isobutyl magnolol
n-BM = n-butyl magnolol
PGMC = propylene glycol monocaprylate Example 2

Samples of the 10 compositions from the preceding example are tested for uptake to Vitro-Skin®. Vitro-Skin® is a testing substrate (available from IMS Technologies) that effectively mimics the surface properties of human skin. It contains both optimized protein and lipid components and is designed to have topography, pH, critical surface tension and ionic strength similar to human skin.

The protocol for the uptake assay is as follows:
1. Cut Vitro-skin (IMS Inc., Portland, Me.) into uniform circles of diameter between 10 to 14 mm. Cork borer may be used. The exact diameter is necessary to calculate uptake per square centimeter.
2. To remove the silicone coating, rinse the Vitro-skin circles (in bulk) 3 times with hexanes for 5 Minutes. Air dry to evaporate hexanes.
3. Soak VitroSkin in sterilized and cleared saliva overnight in disposable polystyrene Falcon tube. Use 1 mL of saliva per tissue. Perform in triplicate.
4. Aspirate saliva, add 1 mL of 1:2 paste slurry and incubate for 2 minutes in 37° C. water bath. Operate quickly as uptake depends on exposure time at all temperatures.
5. Aspirate the slurry and rinse 3-times with 5 mL of deionized water for 10 seconds each. Use vortex for rinsing (max speed). Transfer the tissue into new polystyrene Falcon tube. Operate quickly and process all samples at the same speed.
6. Add 1 mL of ethanol and extract the active thoroughly (vortex or shake for a minimum of 1 hour). The vitroskin doe not dissolve in ethanol.
7. Transfer the extract into an HPLC vial and perform HPLC analysis using appropriate conditions for the specific Active. The obtained level of Active (typically in μg/mL) equals numerically to the pig per tissue (UT).

8. To calculate uptake of Active per square centimeter, use the following formula:

$$UR = 2*UT/(\pi*d2) \ [\mu g/cm2]$$

where:
UR is (relative) uptake of Active per square centimeter of Vitro-skin (both sides)
UT is uptake of Active per tissue
π is 3.14159 . . .
d is diameter of the tissue in centimeters.

Data for the average uptake of isobutyl magnolol and n-butyl magnolol in the Vitro-Skin® assay for the 10 compositions of Example I are set forth in Table 2 (below):

TABLE 2

| Formula from Ex. 1 | Levels of BM, IBM and PGMC | Average IBM uptake (μg/cm²) | Std Dev (μg/cm²) | Average n-BM uptake (μg/cm²) | Std Dev (μg/cm²) |
|---|---|---|---|---|---|
| 1 | 1.0% IBM, 0.0% n-BM | 2.91 | 0.62 | 0.00 | 0.00 |
| 2 | 0.75% IBM, 0.25% n-BM | 2.86 | 0.16 | 2.57 | 0.25 |
| 3 | 0.5% IBM, 0.5% n-BM | 4.97 | 0.45 | 5.33 | 0.70 |
| 4 | 0.25% IBM, 0.75% n-BM | 2.45 | 0.24 | 7.91 | 0.89 |
| 5 | 0.0% IBM, 1.0% n-BM | 0.00 | 0.00 | 17.85 | 0.48 |
| 6 | 1.0% IBM, 0.0% n-BM, 1% PGMC | 2.05 | 0.37 | 0.00 | 0.00 |
| 7 | 0.75% IBM, 0.25% n-BM, 1% PGMC | 2.46 | 0.20 | 1.07 | 0.10 |
| 8 | 0.5% IBM, 0.5% n-BM, 1% PGMC | 1.79 | 0.16 | 1.82 | 0.14 |
| 9 | 0.25% IBM, 0.75% n-BM, 1% PGMC | 0.70 | 0.13 | 2.20 | 0.39 |
| 10 | 0.0% IBM, 1.0% n-BM, 1% PGMC | 0.00 | 0.00 | 3.40 | 0.26 |

It is seen from these data that the optimal absorption for isobutyl magnolol is when the ratio of isobutyl magnolol to butyl magnolol is 1:1 (composition 3). Even though the absolute amount of isobutyl magnolol in composition 3 is only 0.7%, half of the 1.4% in composition 1, the uptake to the Vitro-skin is significantly higher for composition 3 than for composition 1, showing that the presence of n-butyl magnolol facilitates the uptake of the isobutyl magnolol. When the propylene glycol monocaprylate is present, the optimal ratio of isobutyl magnolol to butyl magnolol shifts to 3:1 (composition 7). Surprisingly, however, the best results are obtained without the propylene glycol ester co-surfactant, as seen by the difference between compositions 1 and 6, 2 and 7, 3 and 8, and 4 and 9.

The increased uptake of isobutyl magnolol to Vitro-skin discovered by the present inventors—and described by the data in the table above—when n-butyl magnolol is added to a composition containing isobutyl magnolol, demonstrates the ability of n-butyl magnolol to enhance the solubility of isobutyl magnolol in the compositions described herein.

The invention claimed is:

1. An oral care composition comprising: isobutyl magnolol; n-butyl magnolol; and an orally acceptable carrier; wherein the n-butyl magnolol is present in an amount effective to solubilize the isobutyl magnolol in the orally acceptable carrier; wherein the ratio by weight of isobutyl magnolol to n-butyl magnolol is from about 3:1 to about 1:3.

2. The composition of claim 1 in the form of a toothpaste.

3. The composition of claim 1 in the form of a mouthrinse.

4. The composition of claim 1, wherein the isobutyl magnolol is present in an antibacterially effective amount.

5. The composition of claim 4, wherein the isobutyl magnolol is present in the amount of from about 0.1% to about 3% based on the total weight of the composition.

6. The composition of claim 5, wherein the orally acceptable carrier comprises an additional ingredient selected from: polyethylene glycol, a humectant, an anionic surfactant, a fatty acid monoester of propylene glycol, an effective amount of a fluoride ion source, flavoring, an abrasive, and a combination of two or more thereof.

7. The composition of claim 1, comprising the following ingredients by weight:

| | |
|---|---|
| PEG600 | 2-5% |
| isobutyl magnolol | 0.5-3% |
| n-butyl magnolol | 0.5-3% |
| glycerin | 20-30% |

-continued

| | |
|---|---|
| sorbitol | 20-30% |
| sodium saccharine | 0.1-0.7% s |
| sodium fluoride | 0.1-0.7% |
| sodium lauryl sulfate | 1-3% |
| abrasive silica | 0-20% |

8. A method of treatment, prophylaxis or control of a disease or condition of the oral cavity, comprising applying the composition according to claim 1, to the oral cavity of a patient in need thereof.

9. The method of claim 8 wherein the disease or condition of the oral cavity is selected from caries, gingivitis, periodontitis, tooth yellowing and halitosis.

10. A method of enhancing the solubility of an isobutyl magnolol containing oral care composition comprising admixing a solubilizing effective amount of n-butyl magnolol with an orally acceptable carrier comprising isobutyl magnolol, wherein the ratio by weight of isobutyl magnolol to n-butyl magnolol is from about 3:1 to about 1:3.

11. The composition of claim 6, wherein the orally acceptable carrier comprises propylene glycol monocaprylate as an additional ingredient.

12. The composition of claim 1 wherein the ratio of isobutyl magnolol to n-butyl magnolol is 1:1.

13. The composition of claim 7 wherein the ratio of isobutyl magnolol to n-butyl magnolol is 1:1.

14. The composition of claim 1 which does not comprise a propylene glycol ester.

15. The composition of claim 7 which does not comprise a propylene glycol ester.

* * * * *